United States Patent
Mrva et al.

[11] 3,952,065
[45] Apr. 20, 1976

[54] METHOD OF PRODUCING CHLOROBENZENES FROM BENZENE SULPHONYL CHLORIDES

[75] Inventors: Bohumir Mrva, Jur; Josef Macko, Bratislava; Milan Kupcik, Bratislava; Stefan Truchlik, Bratislava, all of Czechoslovakia

[73] Assignee: Vyskumny ustav agrochemickej Technologie, Bratislava-Predmestie, Czechoslovakia

[22] Filed: June 20, 1974

[21] Appl. No.: 481,041

[30] Foreign Application Priority Data
June 25, 1973 Czechoslovakia.............. 4523-73

[52] U.S. Cl.................. 260/612 D; 260/613 D; 260/650 R
[51] Int. Cl.².............. C07C 43/22; C07C 43/28
[58] Field of Search......... 260/650 R, 612 D, 613 D

[56] References Cited
FOREIGN PATENTS OR APPLICATIONS

| | | | |
|---|---|---|---|
| 1,443,829 | 4/1962 | Germany.................. | 260/650 R |
| 720,079 | 4/1942 | Germany.................. | 260/650 R |
| 492,862 | 7/1919 | France.................... | 260/650 R |

*Primary Examiner*—D. Horwitz

[57] ABSTRACT

A method of producing chlorobenzenes from benzene sulphonyl chlorides by a thermal chlorinating decomposition of aromatic sulphonyl chlorides of the general formula

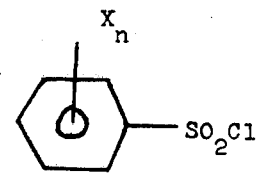

wherein
X = hydrogen, halogen, alkyl group with 1–4 carbon atoms, or alkoxy group with 1–4 carbon atoms, and
n = an integer of from 1 to 5,
in the presence of a catalyst including a combination of active carbon and compounds selected from the group consisting of phosphorus chlorides, phosphorus bromides, and organic azo compounds capable of yielding free radicals when degrading.

1 Claim, No Drawings

METHOD OF PRODUCING CHLOROBENZENES FROM BENZENE SULPHONYL CHLORIDES

BACKGROUND OF THE INVENTION

The present invention relates to a method of preparing substituted chlorobenzene derivatives by a thermal chlorinating decomposition of the corresponding aromatic sulphonyl chlorides.

The thermal chlorinating decomposition of aromatic sulphonyl chlorides in the presence of chlorine, wherein chlorine is substituted for sulphonyl chloride group has been known for many years in the professional literature (German Pat. No. 234,290, BASF: Frdl. 10, 116; German Pat. No. 98,433, Soc. Chim.; Frdl. 5, 41). Due to its availability and the ease of practicing such process, this process has become a preferred method of preparing compounds which are otherwise difficult to obtain. Although the yields attained, which rarely have exceeded 80 percent of the theoretical value, were relatively high, there have been continued attempts to raise these yields.

Because of a radical exchange mechanism during the reaction, experiments have been made as to how to catalyze it, either by illumination or exposure (H. Kroepelin Et Al: Ang. Ch. 64, 274, 1952; B. Miller, C. Walling: J. Am. Chem. Soc. 79, 4187, 1957) or by means of another catalyst capable of accelerating the radical exchange in the reaction, such as, for example, some organic compounds yielding free radicals upon their own degradation. (W. Davies, J. H. Dick: J. Chem. Soc. 1932, 2042; K. Kobaya, N. Ishino: Japanese Pat. No. 13971/62). In this manner, the aforementioned attempts have been successful in some cases with a resulting increase in yield, but in the event an aryl group additionally binds an alkyl group, in the latter of which the complete substitution of chlorine for all the present hydrogen atoms may take place in the final stage, the yields have not been higher than 90 percent of the theoretical yield. Another disadvantage of the above-described process is that the chlorination has been extremely time-consuming (requiring up to 30 hours).

The purpose of the present invention and the basic object of the same is to overcome the aforementioned disadvantages and significantly to improve the method of producing chlorobenzenes from benzene sulphonyl chlorides.

SUMMARY OF THE INVENTION

It has now surprisingly been found out that a thermal chlorinating decomposition of aromatic sulphonyl chlorides of the general formula

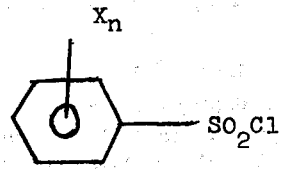

in which X can represent hydrogen, halogen, alkyl with 1–4 carbon atoms, or an alkoxy group with 1–4 carbon atoms in alkyl, and in which $n$ represents an integer of from 1 to 5, by the method of the invention can be substantially accelerated together with simultaneously raising the selectivity of reaction giving rise to the correspondingly substituted chlorobenzenes; in such method the chlorination takes place in the presence of catalysts constituted by a combination of active carbon and compounds selected from the group consisting of phosphorus chlorides, phosphorous bromides, and azo compounds, which catalysts are capable of supplying free radicals.

In accordance with the invention, the reaction may preferably proceed at a temperature range of from 50° to 250°C, the preferable catalyst amount varying from 0.1 to 10 percent by weight relative to the starting sulphonyl chloride amount, and the mutual ratio of the two said catalyst constituents to each other varying from 0.1 : 9.9 to 9.9 : 0.1.

In this way the reaction time can be substantially shortened, while by suppressing side reactions the yields of the obtained correspondingly substituted chlorobenzenes are practically quantitative, varying mostly within the range of from 97 to 100 percent of the theoretical value.

The active carbon used, preferably in powder form, is added in small amounts only which should not exceed 5 percent by weight (relative to the starting benzene sulphonyl chloride amount), i.e. in an amount less than one percent, as a rule. As catalysts of the radical exchange reaction, it is possible to use phosphorus trichloride, phosphorus pentachloride, phosphorus tribromide, phosphorus pentabromide, or organic azo compounds capable of releasing free radicals when degrading. Similarly as the active carbon constituent, the aforementioned compounds are to be added in small amounts of less than 5 percent, preferably less than 2 percent, calculated on the basis of the weight of the starting material.

As hereinabove set forth, the reaction can be carried out within a relatively broad temperature range. In practice, there can be used temperatures up to the boiling point of the respective chlorobenzene produced, or even higher in case the latter is obtained from the reaction mixture by distillation; in most cases, however, lower temperatures of from 100° to 200°C will be sufficient, depending upon the benzene sulphonyl chloride used, the chlorobenzene produced, and the catalyst employed.

Further, the reaction can be carried out either in the presence of an inert solvent or without it. Suitable solvents for this purpose include lower perchlorinated alkane or alkene derivatives, such as, for example, tetrachloromethane, hexachloroethane, tetrachloroethylene, etc. It is to be noted, however, that a solventless process, as a rule, is carried out more easily and more economically.

The reaction can be carried out in any suitable reaction vessel, such as, for instance, a flask, kettle or column. The reaction can be performed as a one-stage process but, with a better utilization of chlorine in mind, it may be advisable to separate it into two or three successive steps. In this way, while in the first step pure chlorine is dosed, waste gas therefrom consisting of hydrogen chloride, chlorine and sulphur dioxide will be introduced into the second step, such waste gas including only hydrogen chloride and sulphur dioxide. As a result, a theoretical chlorine consumption can be considered, while the respective bicomponent waste gaseous medium arises; such a method is more advantageous from the cost viewpoint.

The following examples are given as illustrative only without, however, limiting the invention to the specific

EXAMPLES I to V

Preparation of p-chlorobenzotrichloride

P-chlorobenzotrichloride was prepared in an electrically heated chlorinating glass tower having a height-/diameter ratio of 30 : 1, provided in its bottom part with a capillary tube for supplying chlorine, and provided in its top part with a thermometer and a reflux condenser. The tower was fed with 190.6 parts by weight of p-toluenesulphochloride, one part by weight of pulverized active carbon and the respective parts by weight given in Table I, below, of phosphorus halides. After the contents of the chlorinating tower had been heated to 140°C, chlorine was supplied thereinto at a rate of 50 parts by weight per hour for 2.5 hours, the temperature having been successively raised to 200°C. Thereafter the chlorine supply rate was reduced to 25 parts by weight per hour, and the chlorination was continued for another 5 hours. After no more hydrogen chloride was found in the waste gas, the reaction was stopped. The overall chlorine consumption in Examples Nos. I through III was 250 to 270 parts by weight. After cooling the contents of the chlorinating tower to 100° C and filtering off the active carbon, technical p-chlorobenzotrichloride was obtained.

The results of the Examples carried out in the above-described manner using various catalysts as well as in the presence of and in the absence of active carbon, respectively, are summarized in the following table:

TABLE I

| Example No. | CATALYST | | P-CHLOROBENZOTRICHLORIDE yield | | | Note |
|---|---|---|---|---|---|---|
| | type | number of wt. parts | wt.parts | purity (%) | theory (%) | |
| 1 | $PCl_3$ | 4 | 231 | 98 | 98.5[a] | technical |
| 2 | $PCl_5$ | 5 | 217 | 100 | 94.3[a] | distilled |
| 3 | $PBr_3$ | 7.9 | 227 | 100 | 98.6[a] | distilled |
| 4 | $PCl_3$ | 4 | 191 | 97.8 | 81.4[b] | distilled |
| 5 | $PCl_5$ | 5 | 186 | 84.9 | 68.7[b] | distilled |

[a] in the presence of active carbon
[b] in the absence of active carbon.

EXAMPLE VI

Preparation of p-chlorobenzotrichloride

The preparation was performed in the apparatus described in Examples I to V. The chlorinating tower was fed with 195 parts by weight of p-toluenesulphonyl chloride (97.6 percent), one part by weight of active carbon, and 0.5 parts by weight of 2,2'-azo-bis-isobutyronitrile. After the contents of the chlorinating tower had been heated to 90°C, it was chlorinated for 1.30 hours at a rate of 50 $Cl_2$ parts by weight per hour, after which the temperature was raised to 110°C; at this time 2,2'-azo-bix-isobutyronitrile began to be added to the reaction mixture in small doses at 10 – 15 minute intervals. After 2.5 hours chlorination, the chlorine supply rate was reduced to 25 parts by weight per hour and the chlorination was continued for another 5 hours. After the chlorination was finished, the total consumption of chlorine was found to be 240 – 250 parts by weight and the catalyst consumption to be 1.5 parts by weight. After cooling the reaction mixture to 90°C and filtering off the active carbon, there was obtained 234 parts by weight of technical p-chlorobenzotrichloride having a purity of 96.1 percent, i.e. 97.7 percent in theory.

EXAMPLE VII

Preparation of o-chlorobenzalchloride

The chlorinating tower referred to in the preceding Examples was fed with 190.6 parts by weight of o-toluenesulphonylchloride, one part by weight of active carbon, and 4 parts by weight of phosphorus trichloride. The chlorination was carried out for 7 hours at a temperature within the range of from 140° – 180°C. After cooling and filtering off the active carbon, there was obtained 197 parts by weight of technical o-chlorobenzalchloride containing a small admixture of o-chlorobenzotrichloride.

EXAMPLE VIII

Preparation of 2,4-dichlorobenzotrichloride

The above-described chlorinating tower was fed with 225.1 parts by weight of 2-chloro-p-toluenesulphonylchloride, one part by weight of active carbon, and 4 parts by weight of phosphorus trichloride. The chlorination was carried out for 8 hours at a temperature range of from 140° – 210°C. After cooling and filtering off the active carbon, there was obtained 264 parts by weight of technical 2,4-dichlorobenzotrichloride having a small admixture of 2,4-dichlorobenzalchloride.

EXAMPLE IX

Preparation of chlorobenzene

A reaction flask equipped with a thermometer, an agitator, a reflux condenser and a capillary tube for supplying chlorine was fed with 176 parts by weight of benzenesulfochloride, 4 parts by weight of phosphorus trichloride, and 1.5 parts by weight of active carbon. Chlorine was supplied to the flask for 5 hours at a temperature of from 170° – 180°C, the chlorobenzene arising from the reaction having been distilled via the condenser. In the flask there remained 28 parts by weight of benzene sulphonyl chloride, and there was obtained 82 parts by weight of chlorobenzene which, after having been washed with water and distilled, has $n_D^{20}$ - 1.5248 (lit. 1.5248) which constituted 87 percent yield.

EXAMPLE X

Preparation of p-dichlorobenzene

The chlorinating tower described in Examples I to V was fed with 31.6 parts by weight of p-chlorobenzenesulphonylchloride, 0.5 parts by weight of 2,2'-azo-bix-isobutylnitrile, and one part by weight of active carbon, together with 170 parts by weight of tetra-chloromethane. After the contents of the chlorinator had been heated to a weak reflux, chlorine began to be supplied thereto at a rate of from 5 – 7 parts by weight per hour. Simultaneously there was added dropwise from a separatory funnel a solution of 0.5 parts by weight of 2,2'-azo-bis-isobutylnitrile in 50 vol. parts of tetrachloromethane until sulphur dioxide together with waste gas was found escaping. The reaction time was from 3 – 3.5 hours. After cooling the reaction mixture, active carbon was filtered off, tetrachloromethane was distilled off, after which 20.6 parts by weight of p-dichlorobenzene, i.e. 93.5 percent in theory, was obtained. (Mix melting point together with p-dichlorobenzene amounted to 52° – 53°C; the amount of sulphur dioxide separated in the waste gas was theoretically 95 percent).

EXAMPLE XI

Preparation of p-chlorophenyltrichloromethylether

The chlorinating tower referred to in Examples I - V was fed with 41.2 parts by weight p-methoxybenzenesulphonyl chloride dissolved in 150 vol. parts of tetrachloromethane together with one part by weight of active carbon and 0.3 parts by weight of 2,2'-azo-bis-butyronitrile. After the contents of the chlorinator had been heated to a weak reflux, chlorine began to be added at a rate of 15 – 20 parts by weight per hour, a solution of 1.2 parts by weight of 2,2'-azo-bis-isobutyronitrile in 50 vol. parts of tetrachloromethane having been added dropwise from a separatory funnel for seven hours. After cooling the reaction mixture, the active carbon was filtered off, tetrachloromethane was filtered off, after which 48 parts by weight of p-chlorophenyltrichloromethylether with a small admixture of p-chlorophenyldichloromethylether was obtained (melting point 123° – 124°C; the theoretical amount of sulphur dioxide separated in the waste gas was 96.5 percent).

While the invention had been described as embodied in a method of producing chlorobenzenes from benzene sulphonylchlorides, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that from the standpoint of prior art clearly constitute essential characteristics of the generic and specific aspects of this invention and therefore, such adaptations should and are intended to be comprehended within the meaning and range of equivalence of the following claims.

What is claimed as new and desired to be protected by Letters Patent is set forth in the appended claims.

What is claimed is:

1. A method of producing chlorobenzenes from benzene sulphonyl chlorides by a thermal chlorinating decomposition of aromatic sulphonyl chlorides of the general formula

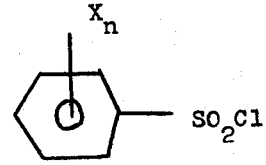

wherein X stands for a radical selected from the group consisting of hydrogen, halogen, alkyl group with 1 – 4 carbon atoms and alkoxy group with 1 – 4 carbon atoms, and $n$ stands for an integer of from 1 to 5, the method comprising carrying out said decomposition at a temperature of from 50° – 250°C in the presence of a catalyst consisting of a combination of active carbon and a compound selected from the group consisting of phosphorus chlorides, phosphorous bromides, and organic azo compounds capable of giving free radicals when degrading, the catalyst being present in an amount of from 0.1 to 10 percent by weight based upon the starting sulphonyl chloride, and the mutual ratio of the two constituents of the catalyst varying between 0.1 : 9.9 and 9.9 : 0.1.

* * * * *